United States Patent
Chiu

(10) Patent No.: US 11,246,510 B2
(45) Date of Patent: Feb. 15, 2022

(54) METHOD AND SYSTEM FOR ANALYZING GAIT OF USER

(71) Applicant: POU CHEN CORPORATION, Chang Hwa Hsien (TW)

(72) Inventor: Hui-Yao Chiu, Taipei (TW)

(73) Assignee: Pou Chen Corporation, Chang Hwa Hsien (TW)

( * ) Notice: Subject to any disclaimer, the term of this patent is extended or adjusted under 35 U.S.C. 154(b) by 129 days.

(21) Appl. No.: 16/802,419

(22) Filed: Feb. 26, 2020

(65) Prior Publication Data

US 2021/0161429 A1 Jun. 3, 2021

(30) Foreign Application Priority Data

Nov. 29, 2019 (TW) .................................. 108143733

(51) Int. Cl.
 *A61B 5/11* (2006.01)
 *A61B 5/00* (2006.01)
 *G01P 13/00* (2006.01)

(52) U.S. Cl.
 CPC ............ *A61B 5/112* (2013.01); *A61B 5/6807* (2013.01); *G01P 13/00* (2013.01); *A61B 5/6829* (2013.01)

(58) Field of Classification Search
 CPC ...... A61B 5/6807; A61B 5/112; A61B 5/6829
 See application file for complete search history.

(56) References Cited

U.S. PATENT DOCUMENTS

| | | | | |
|---|---|---|---|---|
| 2009/0079559 | A1* | 3/2009 | Dishongh | A61B 5/112 340/539.13 |
| 2014/0062703 | A1* | 3/2014 | Purks | A61B 5/1038 340/573.1 |
| 2017/0035330 | A1* | 2/2017 | Bunn | A61B 5/1128 |
| 2017/0273616 | A1* | 9/2017 | Yang | A61B 5/6828 |
| 2017/0354348 | A1* | 12/2017 | Winter | G06F 30/20 |
| 2018/0007277 | A1* | 1/2018 | Aibara | A61B 5/0077 |
| 2019/0389600 | A1* | 12/2019 | Troy | G01N 29/26 |

FOREIGN PATENT DOCUMENTS

| | | |
|---|---|---|
| TW | M562025 U | 6/2018 |
| TW | M562028 U | 6/2018 |

OTHER PUBLICATIONS

Daoud, Foot Strike and Injury Rates in Endurance Runners: A Retrospective Study, Medicine & Science in Sports & Exercise: Jul. 2012—vol. 44—Issue 7—p. 1325-1334 (Year: 2012).*

* cited by examiner

*Primary Examiner* — Michael J Dalbo
(74) *Attorney, Agent, or Firm* — Michael Best & Friedrich LLP

(57) ABSTRACT

A method for analyzing gait of a user includes: detecting, by left and right motion sensors respectively mounted on left and right shoes, movement of the left and right shoes so as to generate and output left-foot motion information and right-foot motion information; and by a processing unit, performing gait analysis based on plural sets of coordinates in a Cartesian coordinate system that are contained in the left-foot motion information and the right-foot motion information so as to generate a result of the gait analysis.

6 Claims, 12 Drawing Sheets

METHOD AND SYSTEM FOR ANALYZING GAIT OF USER

CROSS-REFERENCE TO RELATED APPLICATION

This application claims priority of Taiwanese invention Patent Application No. 108143733, filed on Nov. 29, 2019.

FIELD

The disclosure relates to a method and a system for analyzing gait of a user.

BACKGROUND

A conventional smart insole, such as an intelligent insole module disclosed by Taiwanese Utility Model Patent Application No. M562025 or a conventional smart shoe, such as an intelligent shoes module disclosed by Taiwanese Utility Model Patent Application No. M562028, has a sensor unit disposed therein for collecting motion information.

However, neither the conventional smart insole nor the conventional smart shoe takes into account interactions between both feet of the user. That is to say, the conventional smart insole or shoe performs gait analysis with respect to an individual foot of the user. Therefore, a result of such gait analysis may fail to exactly reflect the gait of the user.

SUMMARY

Therefore, an object of the disclosure is to provide a system and a method for analyzing gait of a user that can alleviate at least one of the drawbacks of the prior art.

According to one aspect of the disclosure, the system includes a pair of shoes, a left motion sensor, a right motion sensor and a processing unit. The pair of shoes include a left shoe to be worn by a left foot of the user and a right shoe to be worn by a right foot of the user. The left motion sensor is mounted on the left shoe, and is configured to detect movement of the left shoe so as to generate left-foot motion information that is related to motion of the left foot of the user, and to output the left-foot motion information. The left-foot motion information contains plural sets of coordinates representing positions of the left shoe in a Cartesian coordinate system. The Cartesian coordinate system is defined by a Z-axis along a vertical direction perpendicular to a horizontal plane, an X-axis perpendicular to the Z-axis and parallel to a direction in which the user is progressing straight, and a Y-axis perpendicular to the X-axis and the Z-axis. The right motion sensor is mounted on the right shoe, and is configured to detect movement of the right shoe so as to generate right-foot motion information that is related to motion of the right foot of the user, and to output the right-foot motion information. The right-foot motion information contains plural sets of coordinates representing positions of the right shoe in the Cartesian coordinate system. The processing unit is configured to perform gait analysis based on the plural sets of coordinates contained in the left-foot motion information and the plural sets of coordinates contained in the right-foot motion information so as to generate a result of the gait analysis.

According to another aspect of the disclosure, the method is adapted to be implemented by the system that is previously described. The method includes steps of:

- by the left motion sensor, detecting movement of the left shoe so as to generate the left-foot motion information, and outputting the left-foot motion information;
- by the right motion sensor, detecting movement of the right shoe so as to generate the right-foot motion information, and outputting the right-foot motion information; and
- by the processing unit, performing the gait analysis based on the plural sets of coordinates contained in the left-foot motion information and the plural sets of coordinates contained in the right-foot motion information so as to generate the result of the gait analysis.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
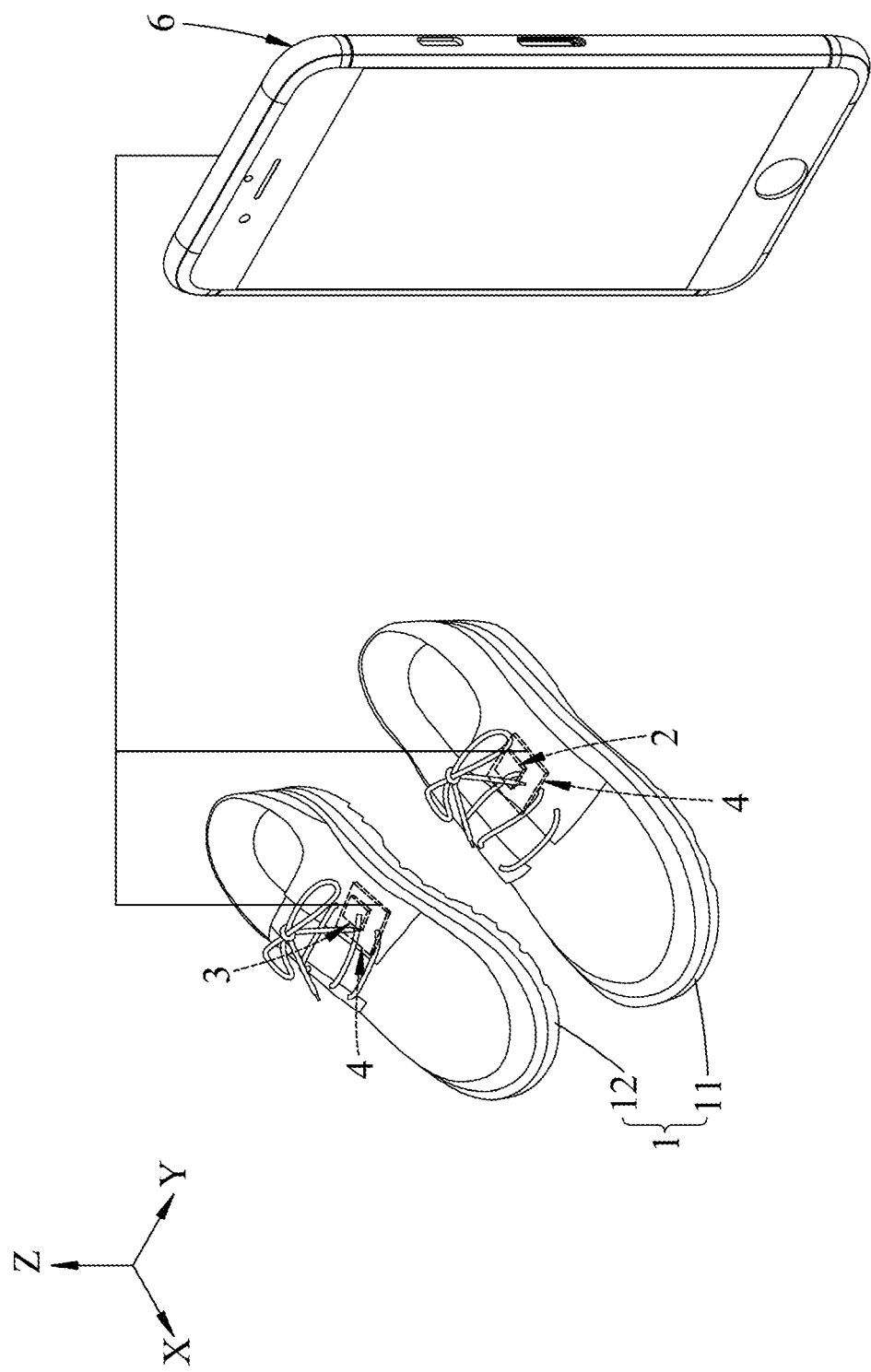
FIG. 1 is a perspective view illustrating an embodiment of a system for analyzing gait of a user according to the disclosure.
Figure 2:
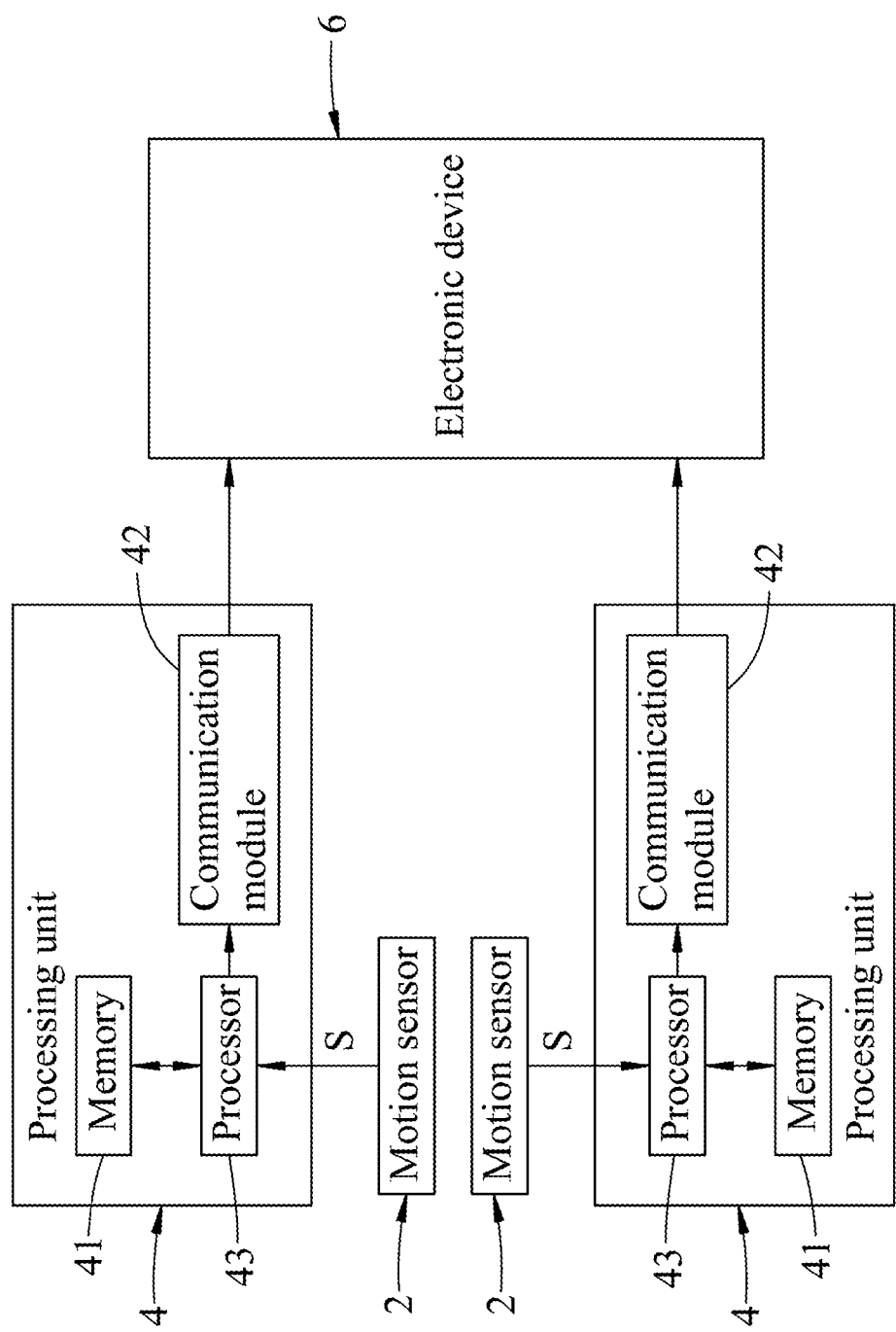
FIG. 2 is a block diagram illustrating the embodiment of the system according to the disclosure.

Referring to FIGS. 1 and 2, an embodiment of a system for analyzing gait of a user according to the disclosure is illustrated. The system includes a pair of shoes 1, a left motion sensor 2, a right motion sensor 3 and two processing units 4.

The pair of shoes 1 include a left shoe 11 and a right shoe 12.

The left motion sensor 2 is mounted on the left shoe 11 to be worn by a left foot of the user, and is configured to detect movement of the left shoe 11 so as to generate left-foot motion information (S1) that is related to motion of the left foot of the user, and to output the left-foot motion information (S1).

The right motion sensor 3 is mounted on the right shoe 12 to be worn by a right foot of the user, and is configured to detect movement of the right shoe 12 so as to generate right-foot motion information (S2) that is related to motion of the right foot of the user, and to output the right-foot motion information (S2). In this embodiment, each of the left motion sensor 2 and the right motion sensor 3 is disposed in a midsole of the respective one of the left and right shoes 11, 12, and is disposed adjacent to the arch of the foot of the user, but may alternatively be disposed in an outsole or attached to an outside surface of the respective one of the left and right shoes 11, 12. Where the left motion sensor 2 and the right motion sensor 3 are mounted are not limited to the disclosure herein and may vary in other embodiments.

In this embodiment, each of the left motion sensor 2 and the right motion sensor 3 is implemented by micro-electromechanical systems (MEMS), and includes a three-axis accelerometer for detecting acceleration on three axes, and a gyroscope for detecting angular speed on the three axes, but implementations of the left motion sensor 2 and the right motion sensor 3 are not limited to the disclosure herein and may vary in other embodiments. Since implementations of the three-axis accelerometer and the gyroscope have been well known to one skilled in the relevant art, detailed explanation of the same is omitted herein for the sake of brevity.

The left-foot motion information (S1) contains plural sets of coordinates representing positions of the left shoe 11 in a Cartesian coordinate system defined by a Z-axis along a vertical direction perpendicular to a horizontal plane, an X-axis perpendicular to the Z-axis and parallel to a direction in which the user is progressing straight when wearing the shoes 1, and a Y-axis perpendicular to the X-axis and the Z-axis. The right-foot motion information (S2) contains plural sets of coordinates representing positions of the right shoe 12 in the Cartesian coordinate system. The origin of the Cartesian coordinate system may be a fixed reference point around the user. Referring to FIGS. 9 to 12, each of the positions of the left shoe 11 and the right shoe 12 is represented by a point "P", and the set of coordinates representing the point "P" in the Cartesian coordinate system is denoted by "P(x,y,z)". Distances, directions and angles of movements of the left shoe 11 and the right shoe 12 are calculated based on trajectories approximating straight lines and derived from the plural sets of coordinates representing positions of the left shoe 11 and the plural sets of coordinates representing positions of the right shoe 12.

The processing units 4 are respectively mounted on the left shoe 11 and the right shoe 12, and are respectively and electrically connected to the left motion sensor 2 and the right motion sensor 3. The processing units 4 are configured to perform gait analysis based on the plural sets of coordinates contained in the left-foot motion information (S1) and the plural sets of coordinates contained in the right-foot motion information (S2) so as to generate a result of the gait analysis.

Each of the processing units 4 includes a memory 41 for storing data, a communication module 42 for establishing communication by means of a set of wireless technologies, and a processor 43 that is electrically connected to the memory 41 and the communication module 42.

The memory 41 stores a threshold value of yaw angle ($\theta10$) and a threshold value of roll angle ($\theta20$). In this embodiment, the memory 41 may be implemented by flash memory, a hard disk drive (HDD) or a solid state disk (SSD), an electrically-erasable programmable read-only memory (EEPROM) or any other non-volatile memory devices, but is not limited thereto.

In this embodiment, the communication module 42 is implemented to be a wireless transceiver that supports wireless communication standards such as Bluetooth technology standards, Wi-Fi wireless networking technologies, or cellular network technology standards such as Narrowband Internet of Things (NB-IoT) and Long-Term Evolution, category M1 (LTE Cat-M1), but is not limited thereto.

In this embodiment, each of the processing units 4 is communicable with an external electronic device 6 (e.g., a smart phone, a tablet computer, or a notebook computer) at a remote location via the communication module 42.

The processor 43 is configured to perform the gait analysis. In this embodiment, the processor 43 may be implemented by a central processing unit (CPU), a microprocessor, a micro control unit (MCU), or any circuit configurable/programmable in a software and/or hardware manner to implement functionalities discussed in this disclosure.

It should be noted that the processing units 4 are communicable with each other via the communication modules 42. The gait analysis may be performed by a specific one of the processing units 4 (e.g., the processing unit 4 disposed on the left shoe 11), or may be cooperatively performed by both of the processing units 4. In the following paragraphs, the gait analysis is exemplarily performed by the processing unit 4 disposed on the left shoe 11.

Figure 3:
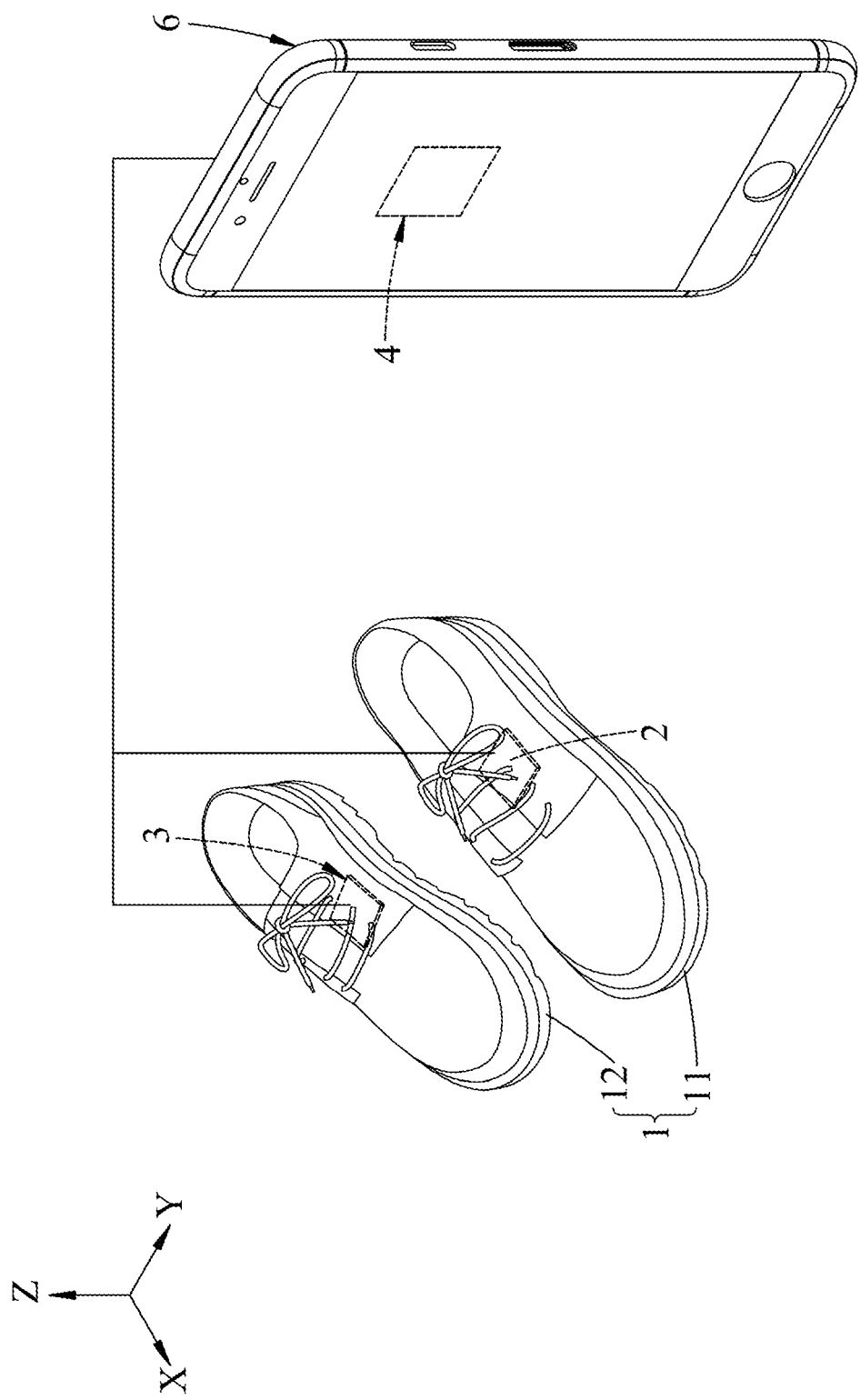
FIG. 3 is a perspective view illustrating another embodiment of the system according to the disclosure.

In one embodiment, there is only one processing unit 4, and the processing unit 4 is separated from the shoes 1. As shown in FIG. 3, the processing unit 4 is integrated in the external electronic device 6, a smart phone. Since integration of a processing unit into an electronic device is well known to one skilled in the relevant art, detailed explanation of the same is omitted herein for the sake of brevity.

Figure 4:
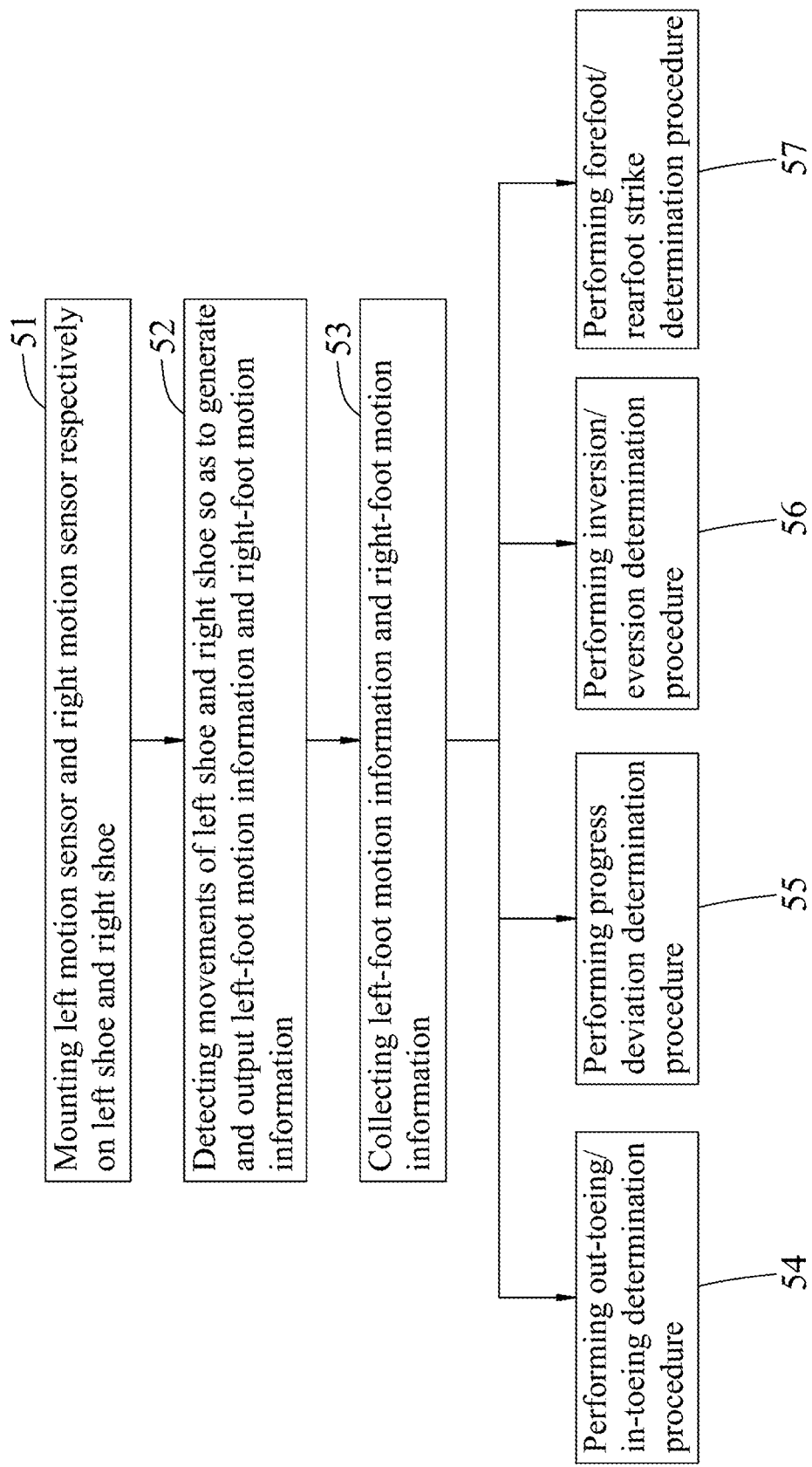
FIGS. 4 to 8 are flow charts illustrating an embodiment of a method for analyzing gait of a user according to the disclosure.

Referring to FIGS. 1, 2 and 4, an embodiment of a method for analyzing gait of a user according to the disclosure is illustrated. The method according to the disclosure is adapted to be implemented by the system that is previously described, and includes steps 51 to 57 outlined below.

In step 51, the left motion sensor 2 is mounted on the left shoe 11, and the right motion sensor 3 is mounted on the right shoe 12.

In step 52, the left motion sensor 2 detects movement of the left shoe 11 so as to generate the left-foot motion information (S1), and outputs the left-foot motion information (S1). Likewise, the right motion sensor 3 detects movement of the right shoe 12 so as to generate the right-foot motion information (S2), and outputs the right-foot motion information (S2). When the user progresses along a line of progression (C) (see FIG. 10), the left-foot motion information (S1) contains the plural sets of coordinates representing the positions of the left shoe 11 during progression of the user, and the right-foot motion information (S2) contains the plural sets of coordinates representing the positions of the right shoe 12 during progression of the user.

In step 53, the processing unit 4 collects the left-foot motion information (S1) and the right-foot motion information (S2) outputted respectively by the left and right motion sensors 2, 3 so as to obtain the sets of coordinates of the points "P".

From steps 54 to 57, the processing unit 4 performs the gait analysis based on the plural sets of coordinates contained in the left-foot motion information (S1) and the plural sets of coordinates contained in the right-foot motion information (S2) so as to generate the result of the gait analysis. In this embodiment, the gait analysis includes an out-toeing/in-toeing determination procedure in step 54, a progress deviation determination procedure in step 55, an inversion/eversion determination procedure in step 56, and a forefoot/rearfoot strike determination procedure in step 57.

Figure 5:
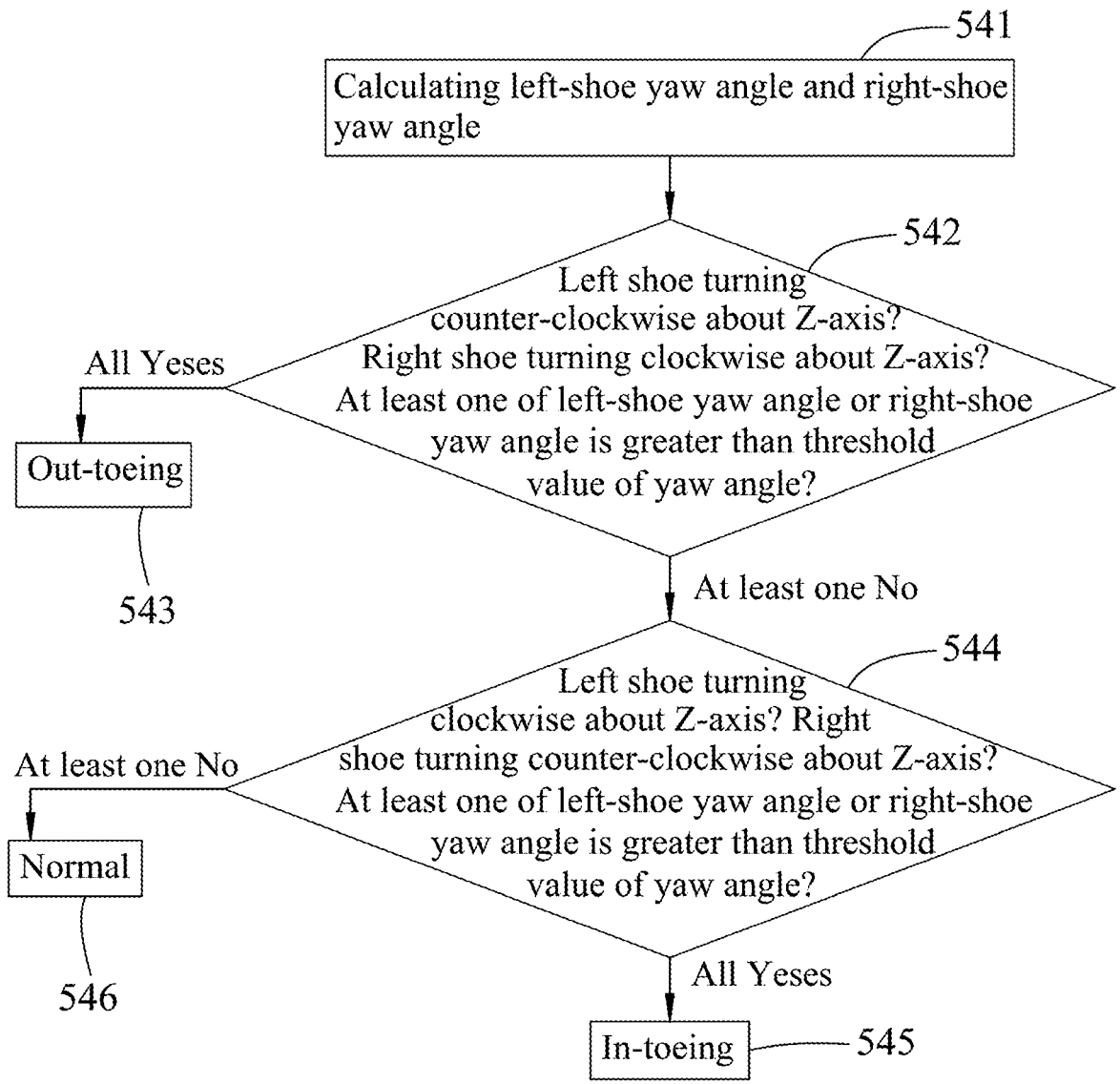

Specifically speaking, referring to FIGS. 5, 9 and 10, the out-toeing/in-toeing determination procedure in step 54 includes sub-steps 541 to 546 outlined below.

In sub-step 541, the processing unit 4 calculates, based on the plural sets of coordinates representing the positions of the left shoe 11, a left-shoe yaw angle (θ11) that is a yaw angle of the left shoe 11 with respect to the X-axis (angle of rotation about the Z-axis), and calculates, based on the plural sets of coordinates representing the positions of the right shoe 12, a right-shoe yaw angle (θ12) that is a yaw angle of the right shoe 12 with respect to the X-axis.

In sub-step 542, based on the left-shoe yaw angle (θ11) and right-shoe yaw angle (θ12), the processing unit 4 determines whether the left shoe 11 is turning about the Z-axis in a counter-clockwise direction when viewed from above, whether the right shoe 12 is turning about the Z-axis in a clockwise direction when viewed from above, and whether at least one of the left-shoe yaw angle (θ11) or the right-shoe yaw angle (θ12) is greater than the threshold value of yaw angle (θ10) (namely one or both of θ11 and θ12 are greater than θ10). When results of all three determinations in sub-step 542 are affirmative, a procedure flow of the method proceeds to sub-step 543. Otherwise, when any of the results is negative, the procedure flow of the method proceeds to sub-step 544.

In sub-step 543, the processing unit 4 determines the gait of the user as out-toeing.

In sub-step 544, the processing unit 4 determines whether the left shoe 11 is turning about the Z-axis in the clockwise direction when viewed from above, whether the right shoe 12 is turning about the Z-axis in the counter-clockwise direction when viewed from above, and whether at least one of the left-shoe yaw angle (θ11) or the right-shoe yaw angle (θ12) is greater than the threshold value of yaw angle (θ10). When results of all three determinations in sub-step 544 are affirmative, the procedure flow proceeds to sub-step 545. Otherwise, when any of the results is negative, the procedure flow of the method proceeds to sub-step 546.

In sub-step 545, the processing unit 4 determines the gait of the user as in-toeing.

In sub-step 546, the processing unit 4 determines the gait of the user as normal, as in no out-toeing or in-toeing.

It should be noted that in one embodiment, both the left-shoe yaw angle (θ11) and the right-shoe yaw angle (θ12) being greater than the threshold value of yaw angle (θ10) is a necessary condition for determining the gait of the user as in-toeing or out-toeing.

Figure 6:
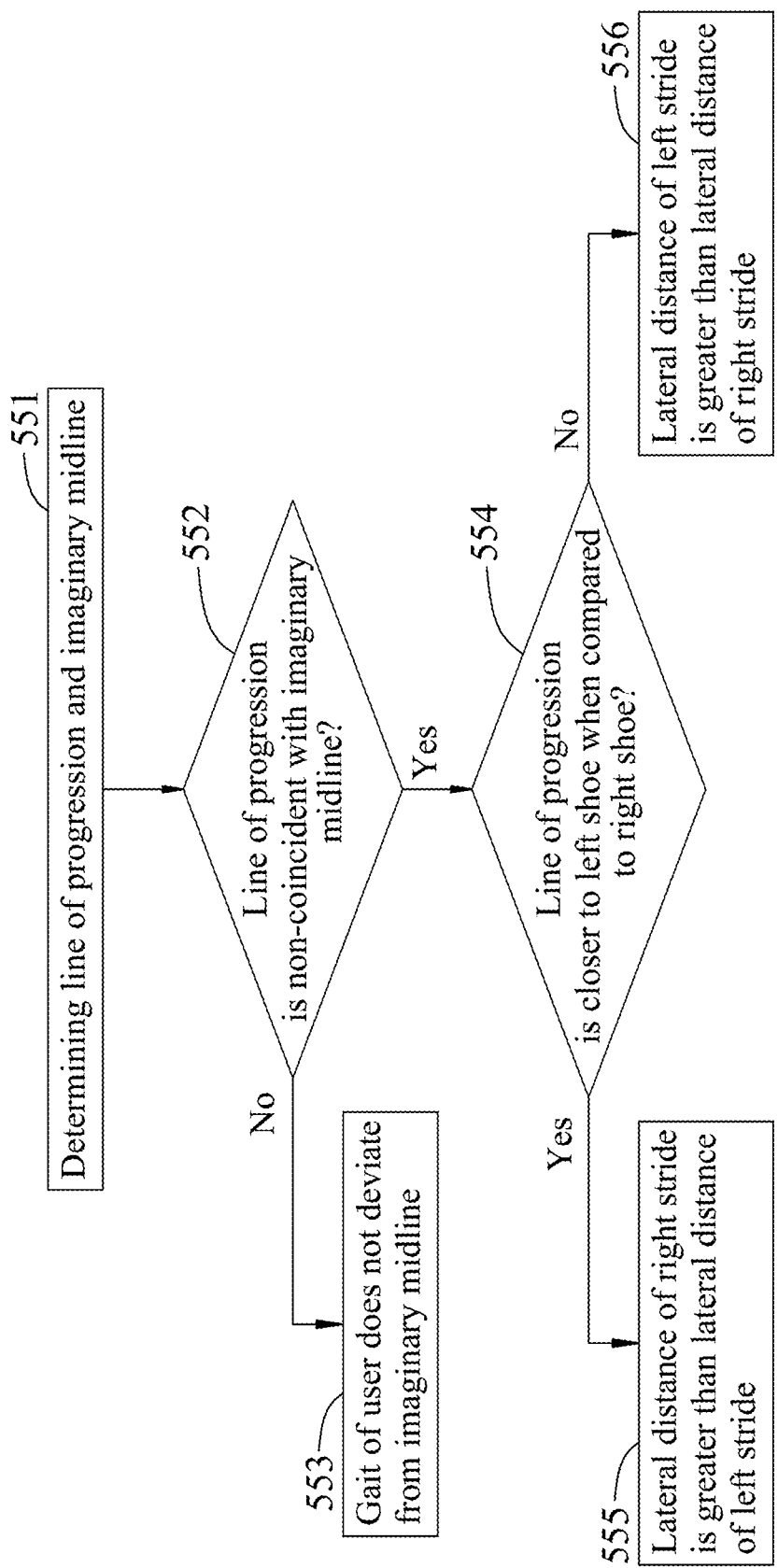
Figure 9:
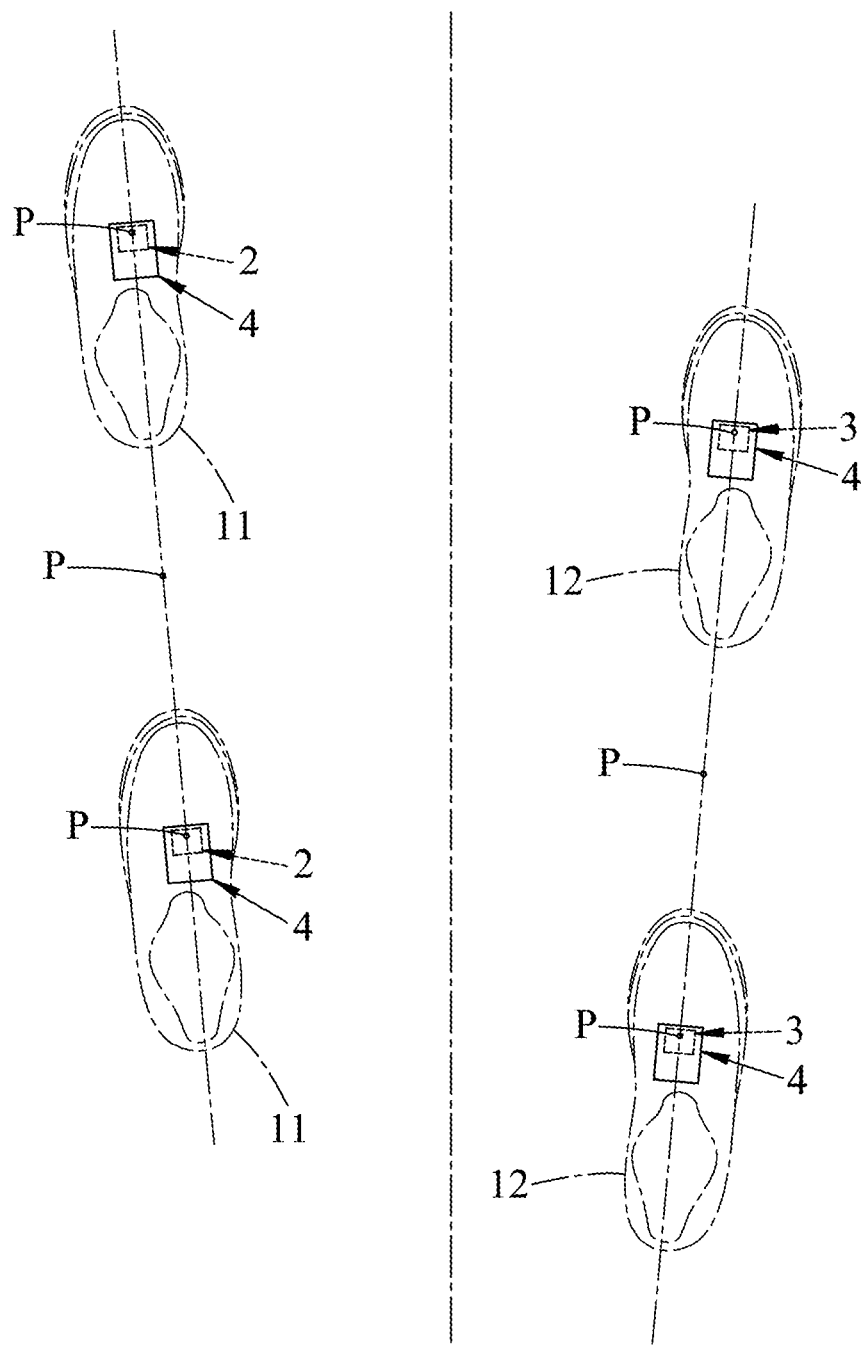
FIG. 9 is a schematic diagram illustrating a series of positions of a left Motion sensor and a right motion sensor of the system according to the disclosure during progression of the user.
Figure 10:
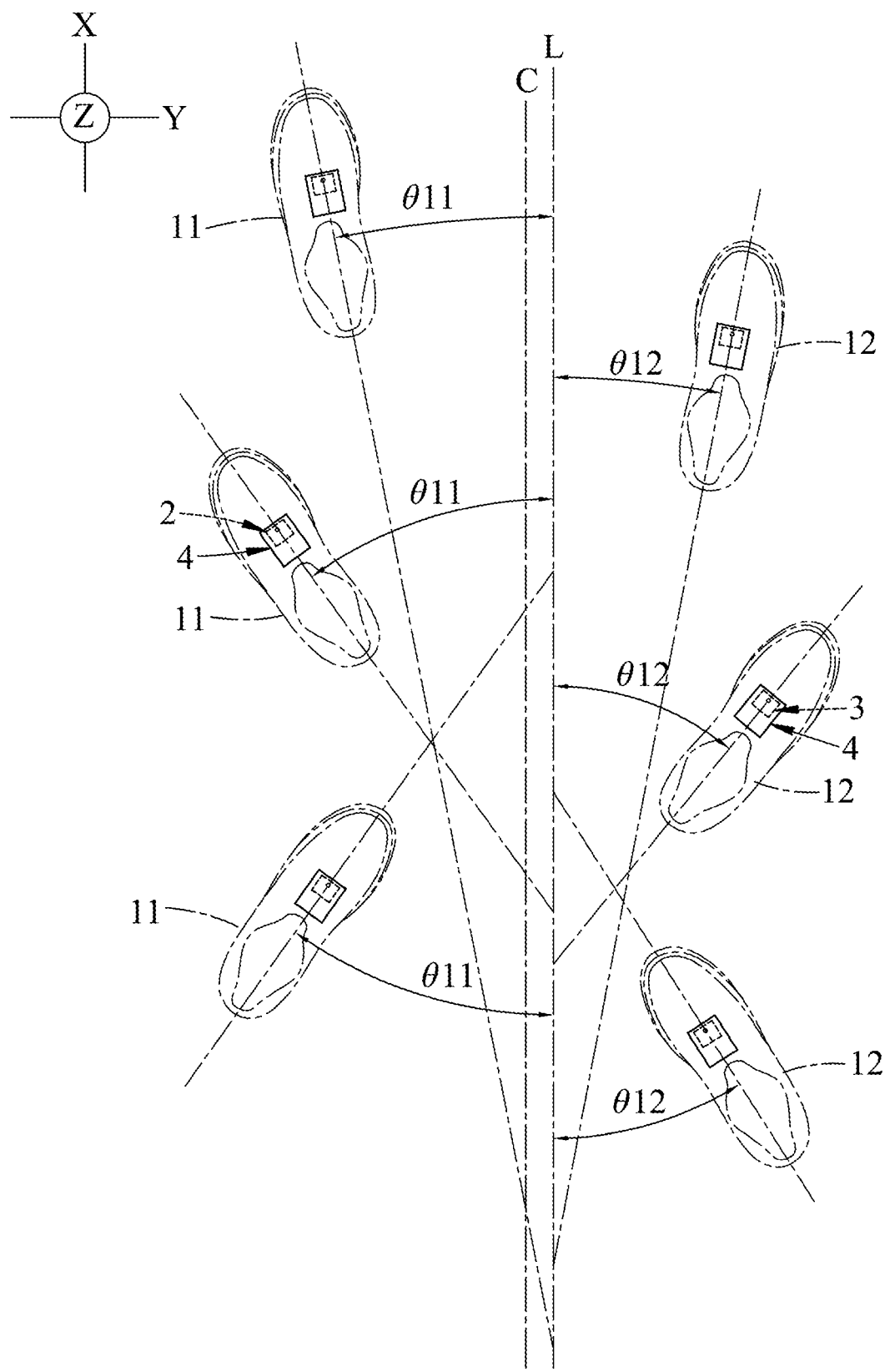
FIG. 10 is a schematic diagram illustrating out-toeing and in-toeing, and deviation of a line of progression determined by the method according to the disclosure.

Referring to FIGS. 6, 9 and 10, the progress deviation determination procedure in step 55 includes sub-steps 551 to 556 outlined below.

In sub-step 551, the processing unit 4 determines, based on the plural sets of coordinates representing the positions of the left shoe 11 and the plural sets of coordinates representing the positions of the right shoe 12, the line of progression (C) and the imaginary midline (L) between the left shoe 11 and the right shoe 12.

In sub-step 552, the processing unit 4 determines whether the line of progression (C) is non-coincident with the imaginary midline (L) in the horizontal plane. When a result of the determination in sub-step 552 is affirmative, the procedure flow of the method proceeds to sub-step 554; otherwise, the procedure flow of the method proceeds to sub-step 553.

In sub-step 553, the processing unit 4 determines that the gait of the user does not deviate from the imaginary midline (L).

In sub-step 554, the processing unit 4 determines whether, between the left shoe 11 and the right shoe 12, the line of progression (C) is closer to the left shoe 11. When a result of the determination in sub-step 554 is affirmative, the procedure flow of the method proceeds to sub-step 555; otherwise, the procedure flow of the method proceeds to sub-step 556.

In sub-step 555, the processing unit 4 determines that a lateral distance of a right stride along the Y-axis is greater than a lateral distance of a left stride along the Y-axis.

In sub-step 556, the processing unit 4 determines that the lateral distance of the left stride is greater than the lateral distance of the right stride.

Figure 7:
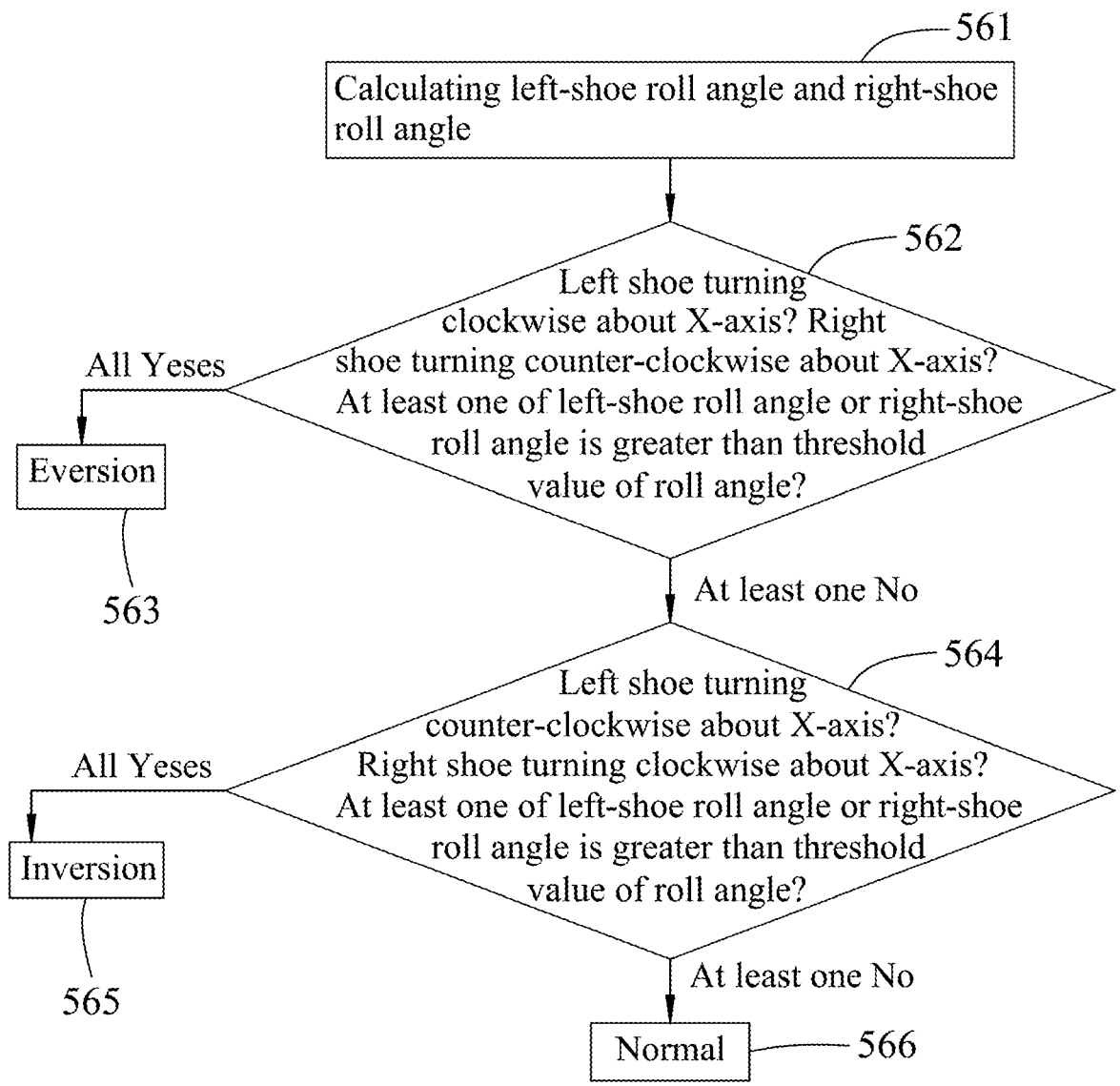
Figure 11:
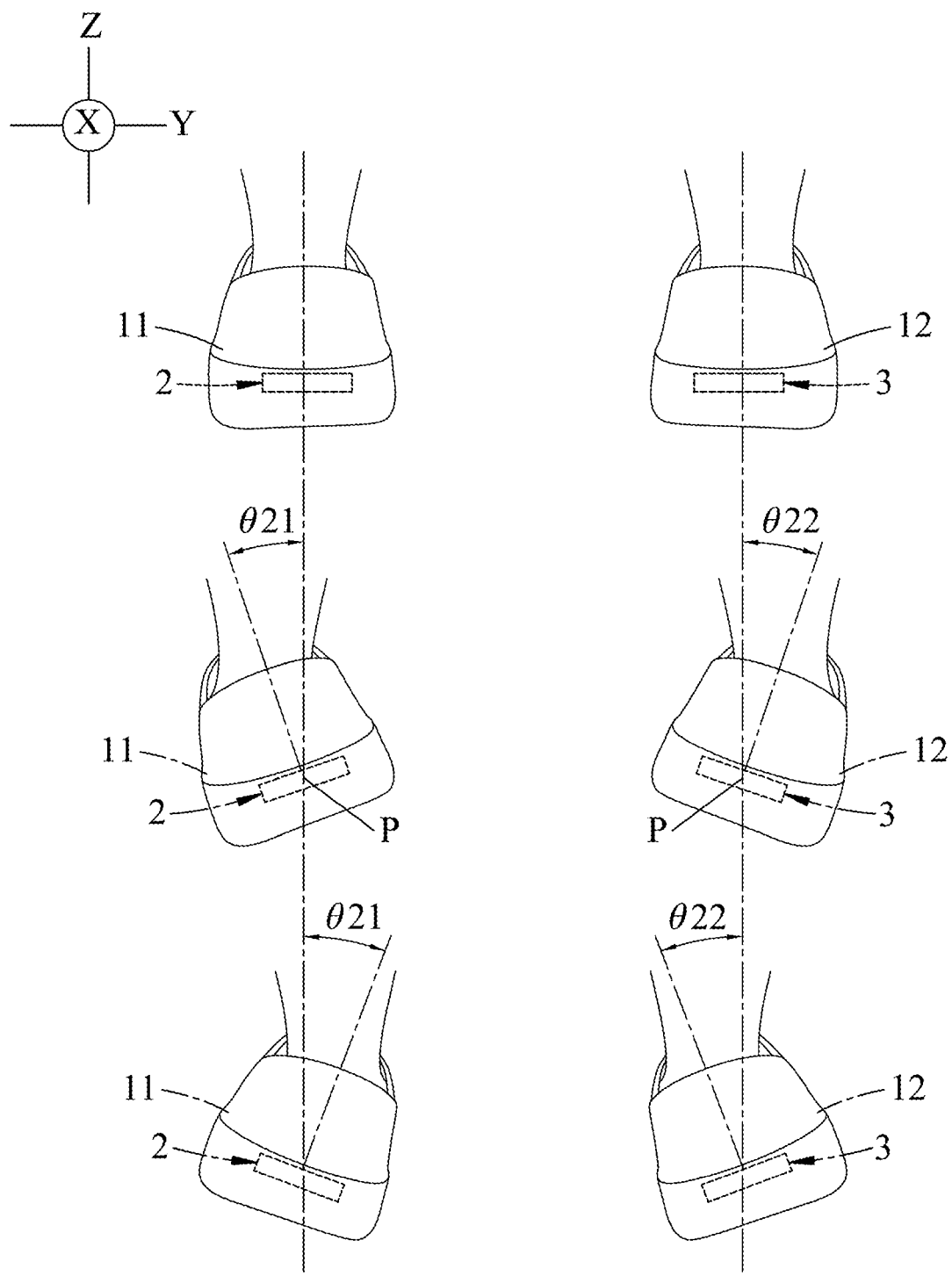
FIG. 11 is a schematic diagram illustrating eversion and inversion. determined by the method according to the disclosure.

Referring to FIGS. 7 and 11, the inversion/eversion determination procedure in step 56 includes sub-steps 561 to 566 outlined below.

In sub-step 561, the processing unit 4 calculates, based on the plural sets of coordinates representing the positions of the left shoe 11, a left-shoe roll angle (θ21) that is a roll angle of the left shoe 11 with respect to the Z-axis, and calculates, based on the plural sets of coordinates representing the positions of the right shoe 12, a right-shoe roll angle (θ22) that is a roll angle of the right shoe 12 with respect to the Z-axis.

In sub-step 562, the processing unit 4 determines whether the left shoe 11 is turning about the X-axis in a clockwise direction when viewed from the back of the user, whether the right shoe 12 is turning about the X-axis in a counter-clockwise direction when viewed from the back of the user, and whether at least one of the left-shoe roll angle (θ21) or the right-shoe roll angle (θ22) is greater than the threshold value of roll angle (θ20) (namely one or both of θ21 and θ22 are greater than θ20). When results of all three determinations in sub-step 562 are affirmative, the procedure flow of the method proceeds to sub-step 563. Otherwise, when any of the results is negative, the procedure flow of the method proceeds to sub-step 564.

In sub-step 563, the processing unit 4 determines the gait of the user as eversion.

In sub-step 564, the processing unit 4 determines whether the left shoe 11 is turning about the X-axis in the counter-clockwise direction when viewed from the back of the user, whether the right shoe 12 is turning about the X-axis in the clockwise direction when viewed from the back of the user, and whether at least one of the left-shoe roll angle (θ21) or the right-shoe roll angle (θ22) is greater than the threshold value of roll angle (θ20). When results of all three determinations in sub-step 564 are affirmative, the procedure flow of the method proceeds to sub-step 565. Otherwise, the procedure flow of the method proceeds to sub-step 566.

In sub-step 565, the processing unit 4 determines the gait of the user as inversion.

In sub-step 566, the processing unit 4 determines the gait of the user is normal, as in no inversion or eversion.

It should be noted that in one embodiment, both the left-shoe roll angle (θ21) and the right-shoe roll angle (θ22) being greater than the threshold value of roll angle (θ20) is a necessary condition for determining the gait of the user as inversion or eversion.

Figure 8:
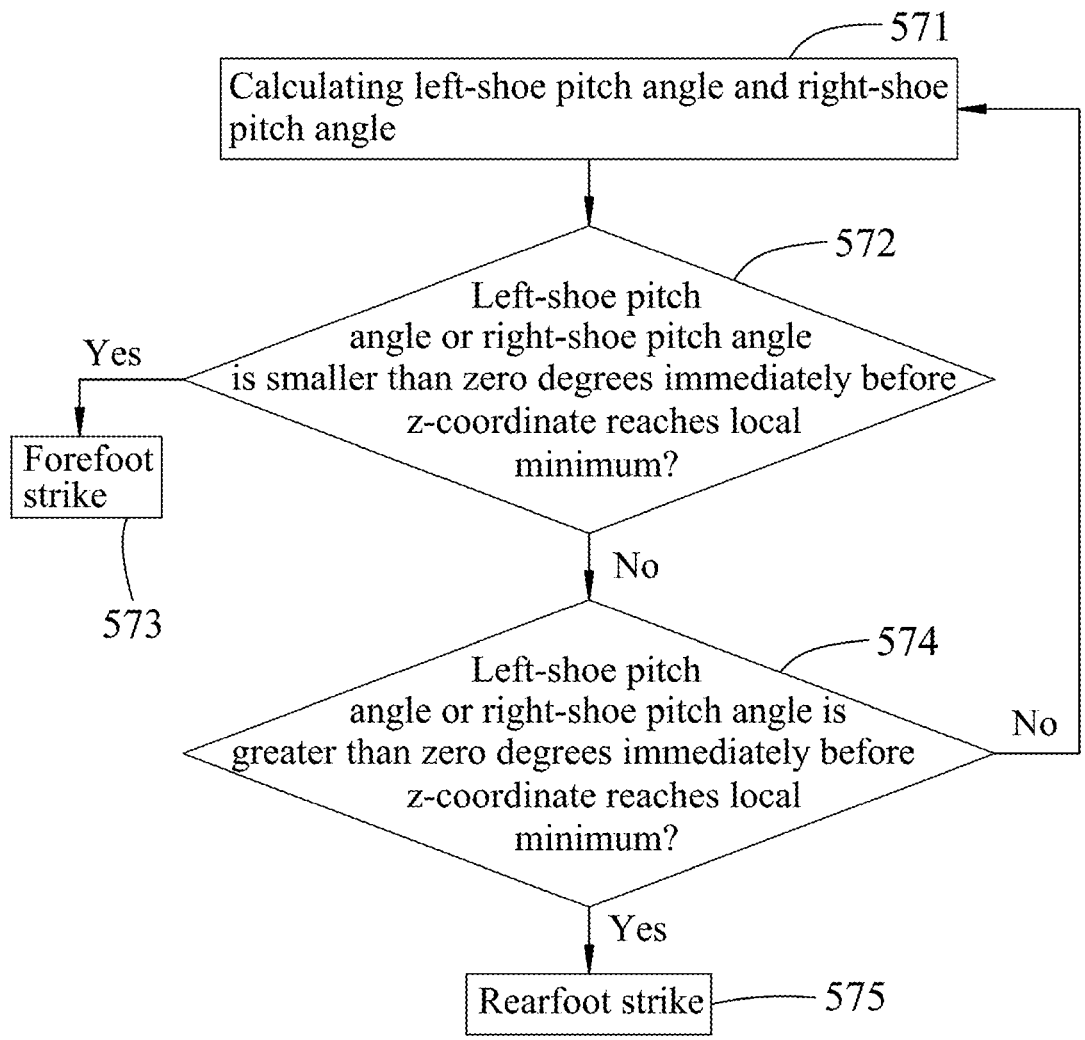
Figure 12:
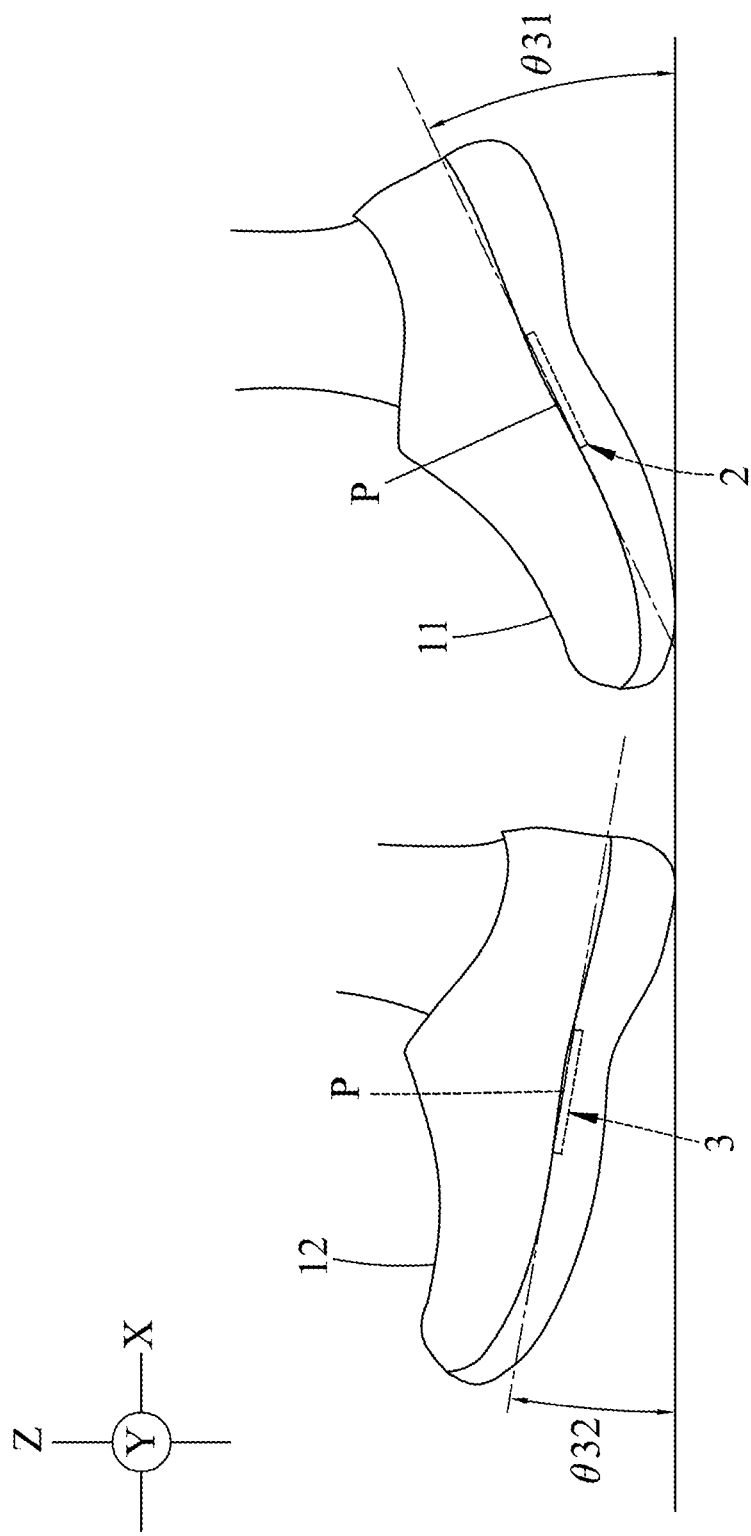
FIG. 12 is a schematic diagram illustrating a forefoot strike and a rearfoot strike determined by the method according to the disclosure.

Referring to FIGS. 8 and 12, the forefoot/rearfoot strike determination procedure in step 57 includes sub-steps 571 to 575 outlined below.

In sub-step 571, the processing unit 4 calculates, based on the plural sets of coordinates representing the positions of the left shoe 11, a left-shoe pitch angle (|31) that is a pitch angle of the left shoe 11 with respect to the horizontal plane, and calculates, based on the plural sets of coordinates representing the positions of the right shoe 12, a right-shoe pitch angle (θ32) that is a pitch angle of the right shoe 12 with respect to the horizontal plane.

In sub-step 572, the processing unit 4 determines whether one of the left-shoe pitch angle ($\theta 31$) and the right-shoe pitch angle ($\theta 32$) is smaller than zero degrees (i.e., whether one of the left shoe and the right shoe pitches down) immediately before a time point when a z-coordinate of the plural sets of coordinates contained in a corresponding one of the left-foot motion information (S1) and the right-foot motion information (S2) reaches a local minimum, where the z-coordinate is equal to zero when the left/right shoe lies flat on the horizontal plane. When a result of the determination in sub-step 572 is affirmative, the procedure flow of the method proceeds to sub-step 573. Otherwise, the procedure flow of the method proceeds to sub-step 574.

In sub-step 573, the processing unit 4 determines that the gait of the user features a forefoot strike (e.g., see the right half of FIG. 12 where the gait features a forefoot strike with the left foot, and the left-shoe pitch angle ($\theta 31$) is smaller than zero degrees).

In sub-step 574, the processing unit 4 determines whether the one of the left-shoe pitch angle and the right-shoe pitch angle is greater than zero degrees (i.e., whether said one of the left shoe and the right shoe pitches up) immediately before the time point when the z-coordinate of the plural sets of coordinates contained in the corresponding one of the left-foot motion information (S1) and the right-foot motion information (S2) reaches a local minimum. When a result of the determination in sub-step 574 is affirmative, the procedure flow of the method proceeds to sub-step 575. Otherwise, the procedure flow of the method returns to sub-step 571.

In sub-step 575, the processing unit 4 determines that the gait of the user features a rearfoot strike (e.g., see the left half of FIG. 12 where the gait features a rearfoot strike with the right foot, and the right-shoe pitch angle ($\theta 32$) is greater than zero degrees).

In summary, the method and the system for analyzing gait of a user utilize the left motion sensor and the right motion sensor respectively mounted on the left shoe and the right shoe of a pair of shoes to detect movement of the shoes so as to generate and output left-foot motion information and right-foot motion information, and utilize the processing unit to perform gait analysis based on plural sets of coordinates that are contained in the left-foot motion information and the right-foot motion information so as to generate a result of the gait analysis. Taking both the left-foot motion information and the right-foot motion information into account in the gait analysis, the result of the gait analysis generated by the method according to the disclosure may truly reflect the gait of the user.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for analyzing gait of a user, to be implemented by a system that includes a left motion sensor mounted on a left shoe that is to be worn by a left foot of the user, a right motion sensor mounted on a right shoe that is to be worn by a right foot of the user, and a processing unit that stores a threshold value of yaw angle, the user progressing along a line of progression, the method comprising:

by the left motion sensor, detecting movement of the left shoe so as to generate left-foot motion information that is related to motion of the left foot of the user, and outputting the left-foot motion information, the left-foot motion information containing plural sets of coordinates representing positions of the left shoe in a Cartesian coordinate system defined by a Z-axis along a vertical direction perpendicular to a horizontal plane, an X-axis perpendicular to the Z-axis and parallel to a direction in which the user is progressing straight, and a Y-axis perpendicular to the X-axis and the Z-axis;

by the right motion sensor, detecting movement of the right shoe so as to generate right-foot motion information that is related to motion of the right foot of the user, and outputting the right-foot motion information, the right-foot motion information containing plural sets of coordinates representing positions of the right shoe in the Cartesian coordinate system; and performing, by the processing unit, gait analysis based on the plural sets of coordinates contained in the left-foot motion information and the plural sets of coordinates contained in the right-foot motion information so as to generate a result of the gait analysis, wherein the performing gait analysis includes calculating, by the processing unit based on the plural sets of coordinates representing the positions of the left shoe, a left-shoe yaw angle that is a yaw angle of the left shoe turning around the Z-axis with respect to the X-axis, calculating, by the processing unit based on the plural sets of coordinates representing the positions of the right shoe, a right-shoe yaw angle that is a yaw angle of the right shoe turning around the Z-axis with respect to the X-axis, determining, by the processing unit, the gait of the user as out-toeing when it is determined that the left shoe is turning around the Z-axis in a counter-clockwise direction from top of the user, that the right shoe is turning around the Z-axis in a clockwise direction from top of the user, and that at least one of the left-shoe yaw angle and the right-shoe yaw angle is greater than the threshold value of yaw angle, and determining, by the processing unit, the gait of the user as in-toeing when it is determined that the left shoe is turning around the Z-axis in the clockwise direction from top of the user, that the right shoe is turning around the Z-axis in the counter-clockwise direction from top of the user, and that at least one of the left-shoe yaw angle and the right-shoe yaw angle is greater than the threshold value of yaw angle, wherein the left-foot motion information contains the plural sets of coordinates representing the positions of the left shoe during progression of the user, wherein the right-foot motion information contains the plural sets of coordinates representing the positions of the right shoe during progression of the user, and wherein the performing gait analysis includes determining, by the processing unit based on the plural sets of coordinates representing the positions of the left shoe and the plural sets of coordinates representing the positions of the right shoe, the line of progression and an imaginary midline between the left shoe and the right shoe, and by the processing unit when it is determined that the line of progression is spaced apart from the imaginary midline, determining that the gait of the user deviates from the imaginary midline, that a lateral distance of a right stride is greater than a lateral distance of a left stride when it is determined that the line of progression is more adjacent to the left shoe than to the right shoe, and that the lateral distance of the left stride is greater than the lateral distance of the right stride when it is determined that the line of progression is more adjacent to the right shoe than to the left shoe.

2. The method as claimed in claim 1, the processing unit storing a threshold value of roll angle, wherein:

the performing gait analysis includes calculating, by the processing unit based on the plural sets of coordinates representing the positions of the left shoe, a left-shoe roll angle that is a roll angle of the left shoe turning around the X-axis with respect to the Z-axis, calculating, by the processing unit based on the plural sets of coordinates representing the positions of the right shoe, a right-shoe roll angle that is a roll angle of the right shoe turning around the X-axis with respect to the Z-axis, determining, by the processing unit, the gait of the user as eversion when it is determined that the left shoe is turning around the X-axis in a clockwise direction from back of the user, that the right shoe is turning around the X-axis in a counter-clockwise direction from back of the user, and that at least one of the left-shoe roll angle and the right-shoe roll angle is greater than the threshold value of roll angle, and determining, by the processing unit, the gait of the user as inversion when it is determined that the left shoe is turning around the X-axis in the counter-clockwise direction from back of the user, that the right shoe is turning around the X-axis in the clockwise direction from back of the user, and that at least one of the left-shoe roll angle and the right-shoe roll angle is greater than the threshold value of roll angle.

3. The method as claimed in claim 1, wherein:

the performing gait analysis includes calculating, by the processing unit based on the plural sets of coordinates representing the positions of the left shoe, a left-shoe pitch angle that is a pitch angle of the left shoe turning around the Y-axis with respect to the horizontal plane, calculating, by the processing unit based on the plural sets of coordinates representing the positions of the right shoe, a right-shoe pitch angle that is a pitch angle of the right shoe turning around the Y-axis with respect to the horizontal plane, determining, by the processing unit, that the gait of the user features a forefoot strike when it is determined that one of the left-shoe pitch angle and the right-shoe pitch angle is smaller than zero degrees immediately before a time point when a z-coordinate of the plural sets of coordinates contained in a corresponding one of the left-foot motion information and the right-foot motion information reaches a local minimum, and determining, by the processing unit, that the gait of the user features a rearfoot strike when it is determined that the one of the left-shoe pitch angle and the right-shoe pitch angle is greater than zero degrees immediately before the time point when the z-coordinate of the plural sets of coordinates contained in the corresponding one of the left-foot motion information and the right-foot motion information reaches a local minimum.

4. A system for analyzing gait of a user, the user progressing along a line of progression, the system comprising:

a pair of shoes including a left shoe to be worn by a left foot of the user and a right shoe to be worn by a right foot of the user;

a left motion sensor mounted on said left shoe, and configured to detect movement of said left shoe so as to generate left-foot motion information that is related to motion of a left foot of the user, and to output the left-foot motion information, the left-foot motion information containing plural sets of coordinates representing positions of said left shoe in a Cartesian coordinate system defined by a Z-axis along a vertical direction perpendicular to a horizontal plane, an X-axis perpendicular to the Z-axis and parallel to a direction in which the user is progressing straight, and a Y-axis perpendicular to the X-axis and the Z-axis;

a right motion sensor mounted on said right shoe, and configured to detect movement of said right shoe so as to generate right-foot motion information that is related to motion of the right foot of the user, and to output the right-foot motion information, the right-foot motion information containing plural sets of coordinates representing positions of said right shoe in the Cartesian coordinate system; and a processing unit configured to perform gait analysis based on the plural sets of coordinates contained in the left-foot motion information and the plural sets of coordinates contained in the right-foot motion information so as to generate a result of the gait analysis, wherein said processing unit is further configured to store a threshold value of yaw angle, calculate, based on the plural sets of coordinates representing the positions of said left shoe, a left-shoe yaw angle that is a yaw angle of said left shoe with respect to the X-axis, calculate, based on the plural sets of coordinates representing the positions of said right shoe, a right-shoe yaw angle that is a yaw angle of said right shoe with respect to the X-axis, determine the gait of the user as out-toeing when it is determined that said left shoe is turning about the Z-axis in a counter-clockwise direction when viewed from above, that said right shoe is turning about the Z-axis in a clockwise direction when viewed from above, and that at least one of the left-shoe yaw angle or the right-shoe yaw angle is greater than the threshold value of yaw angle, and determine the gait of the user as in-toeing when it is determined that said left shoe is turning about the Z-axis in the clockwise direction when viewed from above, that said right shoe is turning about the Z-axis in the counter-clockwise direction when viewed from above, and that at least one of the left-shoe yaw angle or the right-shoe yaw angle is greater than the threshold value of yaw angle, wherein the left-foot motion information contains the plural sets of coordinates representing the positions of said left shoe during progression of the user, wherein the right-foot motion information contains the plural sets of coordinates representing the positions of said right shoe during progression of the user, and wherein said processing unit is further configured to
determine, based on the plural sets of coordinates representing the positions of said left shoe and the plural sets of coordinates representing the positions of said right shoe, the line of progression and an imaginary midline between said left shoe and said right shoe, and when it is determined that the line of progression is non-coincident with the imaginary midline in the horizontal plane, determine that the gait of said user deviates from the imaginary midline, that a lateral distance of a right stride is greater than a lateral distance of a left stride when it is determined that between said left shoe and said right shoe, the line of progression is closer to said left shoe, and that the lateral distance of the left stride is greater than the lateral distance of the right stride when it is determined that between said left shoe and said right shoe, the line of progression is closer to said right shoe.

5. The system as claimed in claim 4, wherein said processing unit is further configured to:

store a threshold value of roll angle;

calculate, based on the plural sets of coordinates representing the positions of said left shoe, a left-shoe roll angle that is a roll angle of said left shoe with respect to the Z-axis;

calculate, based on the plural sets of coordinates representing the positions of said right shoe, a right-shoe roll angle that is a roll angle of said right shoe with respect to the Z-axis;

determine the gait of the user as eversion when it is determined that said left shoe is turning about the X-axis in a clockwise direction when viewed from the back of the user, that said right shoe is turning about the X-axis in a counter-clockwise direction when viewed from the back of the user, and that at least one of the left-shoe roll angle or the right-shoe roll angle is greater than the threshold value of roll angle; and determine the gait of the user as inversion when it is determined that said left shoe is turning about the X-axis in the counter-clockwise direction when viewed from the back of the user, that said right shoe is turning about the X-axis in the clockwise direction when viewed from the back of the user, and that at least one of the left-shoe roll angle or the right-shoe roll angle is greater than the threshold value of roll angle.

6. The system as claimed in claim 4, wherein said processing unit is further configured to:

calculate, based on the plural sets of coordinates representing the positions of said left shoe, a left-shoe pitch angle that is a pitch angle of said left shoe with respect to the horizontal plane;

calculate, based on the plural sets of coordinates representing the positions of said right shoe, a right-shoe pitch angle that is a pitch angle of said right shoe with respect to the horizontal plane;

determine that the gait of the user features a forefoot strike when it is determined that one of the left-shoe pitch angle and the right-shoe pitch angle is smaller than zero degrees immediately before a time point when a z-coordinate of the plural sets of coordinates contained in a corresponding one of the left-foot motion information and the right-foot motion information reaches a local minimum; and determine that the gait of the user features a rearfoot strike when it is determined that the one of the left-shoe pitch angle and the right-shoe pitch angle is greater than zero degrees immediately before the time point when the z-coordinate of the plural sets of coordinates contained in the corresponding one of the left-foot motion information and the right-foot motion information reaches a local minimum.

* * * * *